(12) United States Patent
Segers et al.

(10) Patent No.: US 11,752,222 B2
(45) Date of Patent: Sep. 12, 2023

(54) PREPARATION OF SIZE-CONTROLLED MICROVESICLES

(71) Applicant: Bracco Suisse SA, Cadempino (CH)

(72) Inventors: Tim Segers, Almelo (NL); Emmanuel Gaud, La Croix de Rozon (CH); Gilles Casqueiro, Geneva (CH); Peter Frinking, Laren (NL); Anne Lassus, Carouge (CH)

(73) Assignee: Bracco Suisse SA, Cadempino (CH)

( * ) Notice: Subject to any disclaimer, the term of this patent is extended or adjusted under 35 U.S.C. 154(b) by 50 days.

(21) Appl. No.: 16/978,344

(22) PCT Filed: Mar. 4, 2019

(86) PCT No.: PCT/EP2019/055325
§ 371 (c)(1),
(2) Date: Sep. 4, 2020

(87) PCT Pub. No.: WO2019/170606
PCT Pub. Date: Sep. 12, 2019

(65) Prior Publication Data
US 2021/0000984 A1 Jan. 7, 2021

(30) Foreign Application Priority Data
Mar. 7, 2018 (EP) .................... 18160573

(51) Int. Cl.
*A61K 49/22* (2006.01)
*A61K 47/69* (2017.01)

(52) U.S. Cl.
CPC ........ *A61K 49/223* (2013.01); *A61K 47/6925* (2017.08)

(58) Field of Classification Search
CPC .......................... A61K 49/223; A61K 47/6925
See application file for complete search history.

(56) References Cited

U.S. PATENT DOCUMENTS

| | | | |
|---|---|---|---|
| 10,918,605 B2 | 2/2021 | Segers et al. | |
| 2002/0159951 A1 | 10/2002 | Unger et al. | |
| 2003/0003055 A1 | 1/2003 | Unger et al. | |
| 2003/0175211 A1 | 9/2003 | Schneider et al. | |
| 2006/0034770 A1* | 2/2006 | Schneider | A61K 49/223 424/9.52 |
| 2009/0274628 A1 | 11/2009 | Ottoboni et al. | |
| 2011/0045095 A1* | 2/2011 | Hettiarachchi | A61K 49/225 424/490 |
| 2017/0080113 A1 | 3/2017 | Henriksen et al. | |
| 2018/0008951 A1* | 1/2018 | Van Hoeve | B01F 3/2057 |

FOREIGN PATENT DOCUMENTS

| | | |
|---|---|---|
| CN | 105999314 A | 10/2016 |
| WO | 1995016467 A1 | 6/1995 |
| WO | 9729782 A1 | 8/1997 |
| WO | 2004069284 A2 | 8/2004 |
| WO | 2006018433 A1 | 2/2006 |
| WO | 2013141695 A1 | 9/2013 |
| WO | 2018041906 A1 | 3/2018 |

OTHER PUBLICATIONS

Seo et al., Lab Chip, 2015, 15, p. 3581-3590. (Year: 2015).*
Cander, J. Appl. Physiol., 1959, 14(4), p. 538-540. (Year: 1959).*
Castro-Hernández, et al., "Microbubble generation in a co-flow device operated in a new regime", Lab. Chip., 11:2023-9 (2011).
International Search Report and Written Opinion for PCT/EP2019/055325, dated May 31, 2019.
Segers et al., "Stability of monodisperse phospholipid-coated microbubbles formed by flow-focusing at high production rates," Langmuir 32(16), 3937-3944 (2016).
Shih et al., "Flow-focusing regimes for accelerated production of monodisperse drug-loadable microbubbles toward clinical-scale applications," Lab. Chip, 13:4816-4826 (2013).
Sorgi, Frank L. et al., "Large scale production of DC-Chol cationic liposomes by microfluidization", International Journal of Pharmaceutics, 1996, vol. 144, pp. 131-139, Elsevier Science BV.
Utada, Andrew S. et al., "Dripping to Jetting Transitions in Coflowing Liquid Streams", Physical Review Letters, Aug. 31, 2007, vol. 99, pp. 094502-1-094502-4, The American Physical Society.
Van Hoeve, Wim et al., "Microbubble formation and pinch-off scaling exponent in flow-focusing devices", Physics of Fluids, 2011, vol. 23, pp. 092001-1-092001-8, American Institute of Physica.
Hettiarachchi, et al. "On-chip generation of microbubbles as a practical technology for manufacturing contrast agents for ultrasonic imaging," Lab Chip, 7:463-468 (2007).

* cited by examiner

*Primary Examiner* — Michael G. Hartley
*Assistant Examiner* — Leah H Schlientz
(74) *Attorney, Agent, or Firm* — VIVICAR LAW, PLLC

(57) ABSTRACT

A method for preparing a suspension of "size-controlled" gas-filled microvesicles by microfluidic manufacturing techniques, which comprises using a gaseous flow comprising a first gas having high solubility in water and a second gas having low 5 solubility in water.

14 Claims, 6 Drawing Sheets

PREPARATION OF SIZE-CONTROLLED MICROVESICLES

CROSS-REFERENCE TO RELATED APPLICATIONS

This application is the national stage application of corresponding international application number PCT/EP2019/055325, filed Mar. 4, 2019, which claims priority to and the benefit of European application no. 18160573.4, filed Mar. 7, 2018, which is hereby incorporated by reference in its entirety.

TECHNICAL FIELD

The invention relates to a method for preparing size-controlled microvesicles, such as gas-filled microbubbles, in particular by using a flow-focusing device.

BACKGROUND OF THE INVENTION

Gas-filled microvesicles are generally employed as suitable contrast agents in ultrasound imaging techniques, known as Contrast Enhanced Ultrasound (CEUS) Imaging, or in therapeutic applications, e.g. in combination with ultrasound mediated drug delivery. The gas of these microvesicles is typically entrapped or encapsulated in a stabilizing envelope comprising, for instance, emulsifiers, oils, thickeners or sugars. These stabilized gas bubbles (dispersed in a suitable physiological solution) are generally referred to in the art with various terminologies, depending typically from the stabilizing material employed for their preparation; these terms include, for instance, "microspheres", "microbubbles", "microcapsules" or "microballoons", globally referred to here as "gas-filled microvesicles" (or "microvesicles" in short).

Of particular interest are aqueous suspensions of gas-filled microvesicles where the bubbles of gas are bounded, at the gas/liquid interface, by a very thin envelope (film) involving a stabilizing amphiphilic material (typically a phospholipid) disposed at the gas to liquid interface. These suspensions are typically prepared by contacting powdered amphiphilic materials, e.g. freeze-dried preformed liposomes or freeze-dried or spray-dried lipid solutions, with air or any other gas, and then with an aqueous carrier, while agitating to generate a suspension of gas-filled microvesicles which can then be administered, preferably shortly after its preparation. The stabilizing layer may comprise, in addition to the above cited phospholipids, also other amphiphilic materials, such as fatty acids.

Conventional methods of preparation generally provide gas-filled microvesicles suspensions having a size distribution with a relatively high polydispersity index (PDI), mathematically defined as the ratio between the standard deviation "s" and the mean size "n" of the population of microvesicles: PDI=s/n*100%. For instance, a typical preparation method may provide microvesicles with a mean diameter of about 2-3 micrometer and a PDI of about 60%. Although microvesicles, and particularly gas-filled microvesicles, with a relatively high PDI (such as 60%) are generally well suited for most of the actual imaging techniques, such PDI may nevertheless still be optimized for said imaging techniques. Moreover, for certain therapeutic ultrasound applications it is preferable to minimize the PDI.

Methods have thus been developed for preparing so-called "size-controlled" or "monodispersed" microvesicles, i.e. gas-filled microvesicles preparations where the PDI is lower than 10%, preferably lower than 5% and even more preferably lower than 2%.

Suitable methods for preparing monodisperse microvesicles include, for instance, the use of microfluidic techniques, typically by using T-junctions or flow-focusing devices. In short, in a flow-focusing device, a flow of a gas component is focused by a flow of a liquid component through a narrow orifice. Typically the liquid component comprises an envelope forming material (typically surfactants such as lipids, including phospholipids and/or fatty acids), which entraps the gaseous component to form the desired gas-filled microvesicles, which are stabilized against coalescence and dissolution by said envelope forming material.

Ref. 2, in the name of the same Applicant relates to a microfluidic manufacturing method which applies controlled temperature conditions for limiting the coalescence phenomenon of the microvesicles at the exit of the manufacturing device, in order to maintain the desired controlled size of the freshly formed microvesicles.

It has however been observed that, even by limiting the coalescence phenomenon with the above method, freshly formed gas-filled microvesicles collected at the end of the manufacturing process may become inherently unstable, resulting in the formation of larger-size microvesicles (with respect to desired the calibrated-size) with consequent increase of the PDI in the population of the formed microvesicles and the eventual possible formation of an undesirable foam-layer of very large microvesicles at the top of the liquid suspension of microvesicles. As illustrated by Ref. 1 such large microbubbles contained in the supernatant foam layer may last few hours until they eventually reduce in size to reach their final stable size (substantially corresponding to the original calibrated size). This PDI increase and the associated foaming phenomenon become particularly relevant when using gases having a low aqueous solubility, such as $SF_6$, $C_3F_8$ or $C_4F_{10}$, which are commonly used for improving the persistence of conventional contrast-agent microbubbles. While both the PDI increase and the associated foaming phenomena are in principle reversible if the suspension is left standing for a sufficient period of time (few hours, generally few days or even longer if kept in a sealed container), the presence of such foam is in any case highly undesirable, as it imposes necessary delays for the use (e.g. administration) of the microvesicles or subsequent post-processing of the produced suspension of microvesicles.

Therefore, a method for rapidly stabilizing gas-filled microvesicles immediately after formation using microfluidic flow focusing, in order to limit or avoid such PDI increase and foaming phenomenon is still needed.

Applicant has now found that by using a mixture of a gas having a low solubility in water and of a gas having a high solubility in water in the manufacturing process, said possible PDI increase and foaming phenomenon can be substantially reduced.

Ref. 2 discloses microbubbles filled with mixtures of gases, particularly mixtures of 59-99.5% of a gas A with relatively high solubility in water and a 41%-0.5% of a gas B with relatively low solubility in water.

SUMMARY OF THE INVENTION

According to a first aspect, the present invention thus relates to a method for preparing a suspension of gas-filled microvesicles which comprises:

providing (i) a gaseous flow and (ii) an aqueous liquid flow comprising a microvesicle-stabilizing material;

directing said gaseous flow and said liquid flow through respective inlet channels towards a contact zone;

directing said gaseous flow and said liquid flow from the contact zone through a calibrated orifice to obtain an aqueous suspension comprising said gas-filled microvesicles; and directing said suspension comprising said microvesicles towards an outlet channel;

wherein said gaseous flow comprises a first gas and a second gas, said first gas having high solubility in water and said second gas having low solubility in water, the volume percentage of said second gas in said gaseous flow being of from 18% to 2%.

Preferably, the volume percentage of said second gas in said gaseous flow is of 15% or lower, more preferably of 13% or lower. The volume percentage shall preferably be of at least 3%, more preferably of at least 5%.

The highly water soluble gas has preferably a solubility in water (defined as Bunsen Coefficient "$\alpha$") higher than 0.01, more preferably higher than 0.1 and even more preferably higher than 0.5. The gas with low solubility in water has preferably a solubility in water of 0.008 or lower, more preferably of 0.001 or lower and even more preferably of 0.0008 or lower. Particularly preferred are gases with a solubility in water of 0.0005 or lower.

After completion of the manufacturing process, the resulting stabilized gas-filled microvesicles typically contain of at least 45% of said second gas (with respect to the total volume of gas), preferably at least 60%.

The microvesicle-stabilizing material is preferably and amphiphilic compound, more preferably a phospholipid.

DETAILED DESCRIPTION OF THE INVENTION

Figure 6:
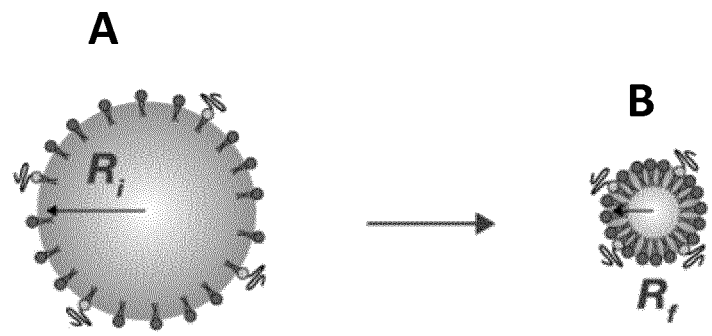
FIG. 6 illustrates a schematic example of size reduction from freshly formed to the final stabilized gas-filled microvesicle.

Gaseous microbubbles prepared according to microfluidics techniques need to be rapidly stabilized against gas dissolution immediately after formation to preserve size monodispersity. Gas dissolution is primarily driven by the Laplace pressure which results from a surface tension between a gas-liquid interface. By adding a suitable microvesicle stabilizer (e.g. an amphiphilic compound, such as phospholipids or fatty acids), the amphiphilic molecules of said compound form a monolayer at the gas-liquid interface resulting in a surface pressure, thus stabilizing the microbubble. In particular, the gaseous content of the freshly formed microvesicles (due, among other, to the relatively loose packing of the layer of amphiphilic molecules around freshly formed microvesicles, see A in FIG. 6) tends however to be partially released (or dissolved) in the surrounding liquid. While the phospholipid monolayer at the gas-liquid interface is mechanically compressed during gas dissolution, it reaches eventually a state with a lipid packing density sufficiently high to create a surface pressure which counterbalances the surface tension and which ultimately stabilizes the microbubble at its final dimension (B in FIG. 6). In some embodiments, the initial radius (Ri) of the freshly formed microvesicles is about twice the final radius (Rf) of the stabilized microvesicles. As mentioned in the above cited paper from T. Segers, the dissolved gas is responsible, through the phenomenon known as "Ostwald ripening", of increasing the polydispersity of the microvesicles suspension, with formation of large microvesicles and ultimately of the foam layer.

Figure 7:
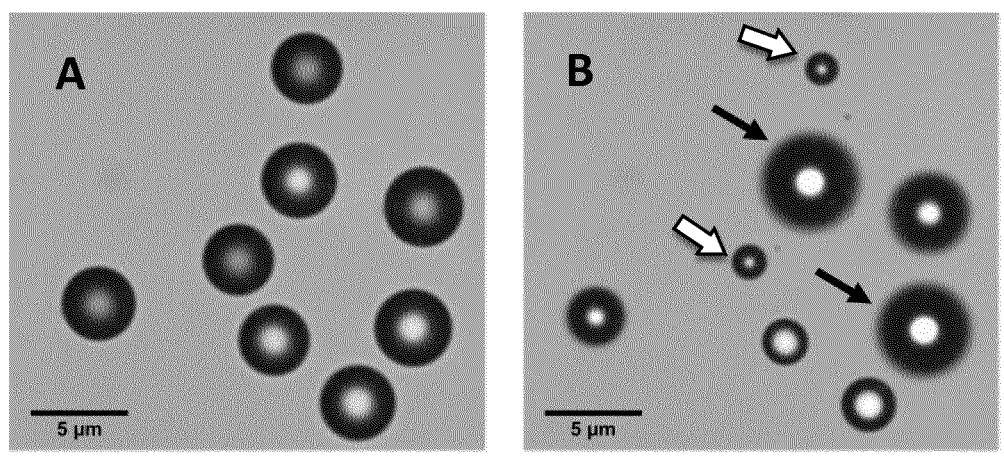
FIG. 7 shows a picture of freshly-formed gas-filled microvesicles prepared with 100% water-insoluble gas and of the respective size modifications during stabilization.

FIG. 7A shows a representative image of freshly-formed phospholipid-stabilized microvesicles obtained by microfluidic flow focusing preparation, by using a gas flow of 100% $C_4F_{10}$ gas; these freshly formed microvesicles were obtained immediately after formation and thus have a substantially uniform size distribution as observable from the image. However, as illustrated in FIG. 7B, during subsequent stabilization after formation, while some microvesicles (indicated by white arrows) rapidly shrink to their final stabilized size of about half the diameter of freshly formed microvesicles, other microvesicles (indicated by black arrows) grow through Ostwald ripening due to inward diffusion of the gas released in the liquid suspension by the shrinking microvesicles (for completeness, also bubbles in an intermediate shrinking or growing phase are observed in FIG. 7B); as a result, polydispersed distribution of microvesicles is observed, with consequent foam formation due to the presence of large size microvesicles.

As mentioned above, while the PDI increase and foam formation associated with the microvesicles growth are generally reversible (so that the final suspension contains substantially monodispersed microvesicles), the size stabilization and disappearance of the foam may however take many hours.

The Applicant has thus found that such PDI increase and foaming phenomenon can be dramatically reduced or substantially avoided by using a suitable mixture of gases as above defined.

Figure 8:
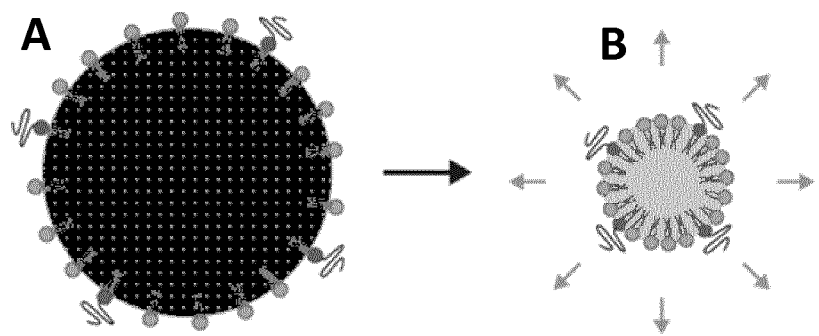
FIG. 8 schematically shows the effect of using a mixture of water-soluble and water-insoluble gases in the preparation of gas-filled microvesicle.

In particular, as illustrated in FIG. 8, the freshly formed microvesicles (A in FIG. 8) comprise a mixture of a gas highly soluble in water ("HS gas", indicated as a black background in the microvesicle of FIG. 8) and of a gas with low solubility in water ("LS gas", indicated in FIG. 8 as grey dots dispersed in the HS gas). During the stabilization phase, the major amount of the highly soluble gas rapidly dissolves in water while the poorly soluble one remains entrapped into the densely packed layer of amphiphilic compounds (B in FIG. 8), typically with some residual amount of HS solubility gas dispersed therein. Differently from the dissolved LS gas (which is released when the microvesicles are prepared with 100% of LS gas) the dissolved HS gas does not trigger any Ostwald ripening, as this gas remains advantageously dissolved in the liquid phase. As observed by the Applicant, the higher the solubility of the HS gas, the lower the foaming phenomenon and PDI increase.

In the present description and claims, the solubility of a gas in water is defined by the Bunsen coefficient "α" of the gas, measured at 25° C. As known in the art, the Bunsen coefficient is a dimensionless value which corresponds to the saturation volume of the gas (reduced to T=273.15° K, p=1 bar) which is absorbed by unit volume of pure solvent at the temperature of measurement and partial pressure of 1 bar.

Suitable HS gases are those gases having a Bunsen coefficient of 0.010 or higher, preferably of 0.100 or higher and even more preferably of 0.500 or higher. These gases have also preferably a relatively low molecular weight, e.g. lower than 80 daltons. Examples of such gases include nitrogen (α=0.0144, Mw 28.01), air (α=0.0167, Mw 28.96) and carbon dioxide (α=0.7614, Mw 44.01), this latter being particularly preferred because of its higher solubility in water.

Suitable LS gases are those having a Bunsen coefficient of 0.0080 or lower, more preferably of 0.0010 or lower and even more preferably of 0.0008 or lower. Particularly preferred are gases with a solubility in water of 0.0005 or lower. These gases have also preferably a relatively high molecular weight, e.g. higher than 120 Daltons, preferably higher than 160 Daltons.

Suitable LS gases include fluorinated gases, preferably perfluorinated gases. Fluorinated gases include materials which contain at least one fluorine atom such as, for instance, fluorinated hydrocarbons (organic compounds containing one or more carbon atoms and fluorine); sulfur hexafluoride; fluorinated, preferably perfluorinated, ketones such as perfluoroacetone; and fluorinated, preferably perfluorinated, ethers such as perfluorodiethyl ether. Preferred compounds are perfluorinated gases, such as $SF_6$ or perfluorocarbons (perfluorinated hydrocarbons), i.e. hydrocarbons where all the hydrogen atoms are replaced by fluorine atoms, which are known to form particularly stable gas-filled microvesicles suspensions.

The term perfluorocarbon includes saturated, unsaturated, and cyclic perfluorocarbons. Examples of biocompatible, physiologically acceptable perfluorocarbons are: perfluoroalkanes, such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes, such as perfluoropropene, perfluorobutenes (e.g. perfluorobut-2ene) or perfluorobutadiene; perfluoroalkynes (e.g. perfluorobut-2-yne); and perfluorocycloalkanes (e.g. perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane). Preferred saturated perfluorocarbons include, for example, $CF_4$, $C_2F_6$, $C_3F_8$, $C_4F_8$, $C_4F_{10}$, $C_5F_{12}$ and $C_6F_{14}$. Particularly preferred gases are those which are in gaseous form at room temperature, including $SF_6$, $C_3F_8$, $C_4F_{10}$.

As observed by the Applicant, by using mixtures of gases with 18% by volume or less (preferably 15% or 13% or less) of a LS gas admixed with a HS gas, the freshly formed microvesicles readily and preferably release the HS gas during stabilization, while the LS gas remains entrapped into the microvesicles. This results in stabilized gas-filled microvesicles with a substantially higher amount of LS contained therein, typically of at least 45% of the total volume of the gas contained in the final stabilized microvesicles, preferably at least 60%. For instance, it has been observed that in certain embodiments (where the volume shrinking from freshly to stabilized microvesicles is of a factor of about 8) microvesicles prepared with a volume content of 13% of LS gas in the preparation's gas-mixture had a concentration of LS gas in the finally stabilized form of about 70%. Similarly, microvesicles prepared with a volume content of 5% of LS gas in the preparation gas-mixture had a concentration of LS gas in the finally stabilized form of about 50%.

On the other side, it has been observed that the volume of the LS gas shall preferably be of at least 2% of the total volume of the preparation gas flow, in order to allow acceptable persistence or values of pressure resistance of the microvesicles (which is generally desired to keep microvesicles circulating once administered and subjected the relatively high blood pressure in the vessels). More preferably the volume of the LS gas in the preparation gas flow shall be of at least 3% of the total volume in the gas, even more preferably of at least 5%.

Microvesicle-Stabilizing Materials

Materials suitable for forming the stabilizing layer of the gas-filled microvesicle (i.e. microvesicles-stabilizing materials) are those known in the art. These preferably include amphiphilic materials. Suitable amphiphilic materials for use in a method of the invention comprise, for instance, phospholipids; lysophospholipids; fatty acids, such as palmitic acid, stearic acid, arachidonic acid or oleic acid; lipids bearing polymers, such as chitin, hyaluronic acid, polyvinylpyrrolidone or polyethylene glycol (PEG), also referred as "pegylated lipids"; lipids bearing sulfonated mono- di-, oligo- or polysaccharides; cholesterol, cholesterol sulfate or cholesterol hemisuccinate;

tocopherol hemisuccinate; lipids with ether or ester-linked fatty acids; polymerized lipids; diacetyl phosphate; dicetyl phosphate; ceramides; polyoxyethylene fatty acid esters (such as polyoxyethylene fatty acid stearates), polyoxyethylene fatty alcohols, polyoxyethylene fatty alcohol ethers, polyoxyethylated sorbitan fatty acid esters, glycerol polyethylene glycol ricinoleate, ethoxylated soybean sterols, ethoxylated castor oil or ethylene oxide (EO) and propylene oxide (PO) block copolymers; sterol esters of sugar acids including cholesterol glucuronides, lanosterol glucuronides, 7-dehydrocholesterol glucuronide, ergosterol glucuronide, cholesterol gluconate, lanosterol gluconate, or ergosterol gluconate; esters of sugar acids and alcohols including lauryl glucuronide, stearoyl glucuronide, myristoyl glucuronide, lauryl gluconate, myristoyl gluconate, or stearoyl gluconate; esters of sugars with aliphatic acids including sucrose laurate, fructose laurate, sucrose palmitate, sucrose stearate, glucuronic acid, gluconic acid or polyuronic acid; saponins including sarsasapogenin, smilagenin, hederagenin, oleanolic acid, or digitoxigenin; glycerol or glycerol monoesters with fatty acids, including glycerol monopalmitate, glycerol monostearate, glycerol monomyristate or glycerol monolaurate, long chain alcohols including n-decyl alcohol, lauryl alcohol, myristyl alcohol, cetyl alcohol, or n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-β-D-mannopyranoside; 12-(((7'-diethylaminocoumarin-3-yl)carbonyl)methyl-amino)octadecanoic acid; N-[12-(((7'-diethylaminocoumarin-3-yl)carbonyl)methylamino)

octadecanoyl]-2-aminopalmitic acid; N-succinyldioleylphosphatidylethanolamine; 1,2-dioleyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine or palmitoylhomocysteine; alkylamines or alkylammonium salts, comprising at least one ($C_{10}$-$C_{20}$), preferably ($C_{14}$-$C_{18}$), alkyl chain, such as, for instance, N-stearylamine, N,N'-distearylamine, N-hexadecylamine, N,N'-dihexadecylamine, N-stearylammonium chloride, N,N'-distearylammonium chloride, N-hexadecylammonium chloride, N,N'-dihexadecylammonium chloride, dimethyldioctadecylammonium bromide (DDAB), hexadecyltrimethylammonium bromide (CTAB); tertiary or quaternary ammonium salts comprising one or preferably two ($C_{10}$-$C_{20}$), preferably ($C_{14}$-$C_{18}$), acyl chain linked to the N-atom through a ($C_3$-$C_6$) alkylene bridge, such as, for instance, 1,2-distearoyl-3-trimethylammonium-propane (DSTAP), 1,2-dipalmitoyl-3-trimethylammonium-propane (DPTAP), 1,2-oleoyl-3-trimethylammonium-propane (DOTAP), 1,2-distearoyl-3-dimethylammonium-propane (DSDAP); and mixtures or combinations thereof.

According to a preferred embodiment, at least one of the compounds forming the envelope of the microvesicles is a phospholipid, optionally in admixture with any of the other above cited materials. According to the present description, the term phospholipid is intended to encompass any amphiphilic phospholipid compound, the molecules of which are capable of forming a stabilizing film of material (typically in the form of a mono-molecular layer), particularly at the gas-water interface in the final microvesicles' suspension. Accordingly, these materials are also referred to in the art as "film-forming phospholipids".

Amphiphilic phospholipid compounds typically contain at least one phosphate group and at least one, preferably two, lipophilic long-chain hydrocarbon group.

Examples of suitable phospholipids include esters of glycerol with one or preferably two (equal or different) residues of fatty acids and with phosphoric acid, wherein the phosphoric acid residue is in turn bound to a hydrophilic group, such a, for instance, choline (phosphatidylcholines—PC), serine (phosphatidylserines—PS), glycerol (phosphatidylglycerols—PG), ethanolamine (phosphatidylethanolamines—PE), inositol (phosphatidylinositol). Esters of phospholipids with only one residue of fatty acid are generally referred to in the art as the "lyso" forms of the phospholipid or "lysophospholipids". Fatty acids residues present in the phospholipids are in general long chain aliphatic acids, typically containing from 12 to 24 carbon atoms, preferably from 14 to 22; the aliphatic chain may contain one or more unsaturations or is preferably completely saturated. Examples of suitable fatty acids included in the phospholipids are, for instance, lauric acid, myristic acid, palmitic acid, stearic acid, arachidic acid, behenic acid, oleic acid, linoleic acid, and linolenic acid. Preferably, saturated fatty acids such as myristic acid, palmitic acid, stearic acid and arachidic acid are employed.

Further examples of phospholipids are phosphatidic acids, i.e. the diesters of glycerol-phosphoric acid with fatty acids; sphingolipids such as sphingomyelins, i.e. those phosphatidylcholine analogs where the residue of glycerol diester with fatty acids is replaced by a ceramide chain; cardiolipins, i.e. the esters of 1,3-diphosphatidylglycerol with a fatty acid; glycolipids such as gangliosides GM1 (or GM2) or cerebrosides; glucolipids; sulfatides and glycosphingolipids.

As used herein, the term phospholipids include either naturally occurring, semisynthetic or synthetically prepared products that can be employed either singularly or as mixtures.

Examples of naturally occurring phospholipids are natural lecithins (phosphatidylcholine (PC) derivatives) such as, typically, soya bean or egg yolk lecithins.

Examples of semisynthetic phospholipids are the partially or fully hydrogenated derivatives of the naturally occurring lecithins. Preferred phospholipids are fatty acids di-esters of phosphatidylcholine, ethylphosphatidylcholine, phosphatidylglycerol, phosphatidic acid, phosphatidylethanolamine, phosphatidylserine, phosphatidylinositol or of sphingomyelin.

Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoyl-phosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP), dilauroyl-phosphatidylinositol (DLPI), diarachidoylphosphatidylinositol (DAPI), dimyristoylphosphatidylinositol (DMPI), dipalmitoylphosphatidylinositol (DPPI), distearoylphosphatidylinositol (DSPI), dioleoyl-phosphatidylinositol (DOPI).

Suitable phospholipids further include phospholipids modified by linking a hydrophilic polymer, such as polyethyleneglycol (PEG) or polypropyleneglycol (PPG), thereto. Preferred polymer-modified phospholipids include "pegylated phospholipids", i.e. phospholipids bound to a PEG polymer. Examples of pegylated phospholipids are pegylated phosphatidylethanolamines ("PE-PEGs" in brief) i.e. phosphatidylethanolamines where the hydrophilic ethanolamine moiety is linked to a PEG molecule of variable molecular weight (e.g. from 300 to 20000 daltons, preferably from 500 to 5000 daltons), such as DPPE-PEG (or DSPE-PEG, DMPE-PEG, DAPE-PEG or DOPE-PEG). For example, DPPE-PEG2000 refers to DPPE having attached thereto a PEG polymer having a mean average molecular weight of about 2000.

Particularly preferred phospholipids are DAPC, DSPC, DPPC, DMPA, DPPA, DSPA, DMPG, DPPG, DSPG, DMPS, DPPS, DSPS and Ethyl-DSPC. Most preferred are DPPG, DPPS and DSPC.

Mixtures of phospholipids can also be used, such as, for instance, mixtures of DPPE and/or DSPE (including pegylated derivatives), DPPC, DSPC and/or DAPC with DSPS, DPPS, DSPA, DPPA, DSPG, DPPG, Ethyl-DSPC and/or Ethyl-DPPC.

For instance, a mixture of phospholipids may include phosphatidylcholine derivatives, phosphatidic acid derivatives and pegylated phosphatidylethanolamine, e.g. DSPC/DPPA/DPPE-PEG, DPPC/DPPA/DPPE-PEG, DSPC/DPPA/DSPE-PEG, DPPC/DPPA/DSPE-PEG, DAPC/DPPA/DPPE-PEG, DAPC/DPPA/DSPE-PEG, DSPC/DSPA/DPPE-PEG, DPPC/DSPA/DSPE-PEG, DSPC/DSPG/DPPE-PEG, DPPC/DSPG/DSPE-PEG.

According to an embodiment of the invention, the phospholipid is the main component of the stabilizing envelope of microvesicles, amounting to at least 50% (w/w) of the total amount of components forming the envelope of the gas-filled microvesicles, preferably at least 75%. In some of the preferred embodiments, substantially the totality of the envelope (i.e. at least 90% w/w) can be formed of phospholipids.

The phospholipids can conveniently be used in admixture with any of the above listed amphiphilic compounds. Thus, for instance, lipids such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof or butylated hydroxytoluene and/or other non-phospholipid compounds can optionally be added to one or more of the foregoing phospholipids, e.g in proportions preferably ranging from zero to 50% by weight, more preferably up to 25%. For instance, mixtures of amphiphilic materials comprising phosphilpids and fatty acids can advantageously be used, including DSPC/DPPG/palmitic acid, DSPC/DPPE-PEG/palmitic acid, DPPC/DPPE-PEG/palmitic acid, DSPC/DSPE-PEG/palmitic acid, DPPC/DSPE-PEG/palmitic acid, DSPC/DPPE-PEG/stearic acid, DPPC/DPPE-PEG/stearic acid, DSPC/DSPE-PEG/stearic acid or DPPC/DSPE-PEG/stearic acid.

The microvesicles prepared according to the method of the invention may optionally comprise a targeting ligand.

The term "targeting ligand" includes within its meaning any compound, moiety or residue having, or being capable to promote, a targeting activity (e.g. including a selective binding) of the microvesicles of a composition of the invention towards any biological or pathological site within a living body. Targets with which targeting ligand may be associated include tissues such as, for instance, myocardial tissue (including myocardial cells and cardiomyocytes), membranous tissues (including endothelium and epithelium), laminae, connective tissue (including interstitial tissue) or tumors; blood clots; and receptors such as, for instance, cell-surface receptors for peptide hormones, neurotransmitters, antigens, complement fragments, and immunoglobulins and cytoplasmic receptors for steroid hormones.

The targeting ligand may be synthetic, semi-synthetic, or naturally occurring. Materials or substances which may serve as targeting ligands include, for example, but are not limited to proteins, including antibodies, antibody fragments, receptor molecules, receptor binding molecules, glycoproteins and lectins; peptides, including oligopeptides and polypeptides; peptidomimetics; saccharides, including mono and polysaccharides; vitamins; steroids, steroid analogs, hormones, cofactors, bioactive agents and genetic material, including nucleosides, nucleotides and polynucleotides.

The targeting ligand may be an amphiphilic compound per se (which is admixed with the other components of the microvesicle) or a compound bound to an amphiphilic molecule (e.g. a phospholipid) employed for the formation of the microvesicles.

In one preferred embodiment, the targeting ligand may be bound to an amphiphilic molecule (e.g. a phospholipid) forming the stabilizing envelope of the microvesicles through a covalent bond. In order to covalently bind a desired targeting ligand, at least part of the amphiphilic compound forming the microvesicle envelope shall thus contain a suitable reactive moiety and the targeting ligand containing the complementary functionality will be linked thereto according to known techniques, e.g. by adding it to a dispersion comprising the amphiphilic components of the microvesicle. Preferably, the amphiphilic compound is a lipid bearing a hydrophilic polymer, such as those previously mentioned, preferably a pegylated phospholipid. In this case, the targeting ligand is linked to a suitable reactive moiety on the hydrophilic polymer. The amphiphilic compound may be combined with the desired targeting ligand before preparing the microvesicle, and the so obtained combination may be used for the preparation of the microvesicle. Alternatively, a microvesicle may first be manufactured, which comprises a compound (lipid or polymer-modified lipid) having a suitable moiety capable of interacting with a corresponding complementary moiety of a targeting ligand; thereafter, the desired targeting ligand is added to the microvesicle suspension, to bind to the corresponding complementary moiety on the microvesicle. According to an alternative embodiment, the targeting ligand may also be suitably associated with the microvesicle via physical and/or electrostatic interactions.

Aqueous Liquid Flow

The aqueous liquid flow for preparing the calibrated gas-filled microvesicles according to the method of the invention comprises an amphiphilic material (as above defined) at a concentration of e.g. from 5.0 to 20 mg/mL, preferably from 7.5 to 15 mg/mL, dispersed in an aqueous carrier.

Suitable aqueous carriers, which are preferably physiologically acceptable, comprise water (preferably sterile water), aqueous solutions such as saline (which may advantageously be balanced so that the final product for injection is not hypotonic), or solutions of one or more tonicity adjusting substances. Tonicity adjusting substances comprise salts or sugars, sugar alcohols, glycols or other non-ionic polyol materials (e.g. glucose, sucrose, sorbitol, mannitol, glycerol, polyethylene glycols, propylene glycols and the like), chitosan derivatives, such as carboxymethyl chitosan, trimethyl chitosan or gelifying compounds, such as carboxymethylcellulose, hydroxyethyl starch or dextran.

In an alternative embodiment, an additional oil phase may be added for incorporating therapeutic hydrophobic substances into the microvesicles. To this end, two additional conduits may be provided in the device for supplying the desired oil phase, as described for instance by Ref. 2. The formed gas-filled microvesicles will thus have a film of oil disposed at the interface between gas and the stabilizing layer of amphiphilic material, which can be loaded with a desired therapeutic agent. Suitable oils may include any biocompatible oil which is liquid at room temperature including, for instance, mono-, di- or tri-esters of glycerol with saturated or unsaturated ($C_2$-$C_{18}$) alkyl chains (including homo- or hetero-allkylesters), such as glycerol monobutyrin, glycerol monolinoleate, 1,2-dihexanoyl glycerol, 1,2 dioctanoyl glycerol, 1,2-dioleyl-sn-glycerol, triacetin, tributyrin, tricaproin, tricaprylin, tricaprin, and mixtures thereof; or natural oils such as soya oil, olive oil, safflower seed oil, sunflower seed oil, peanut oil and mixtures thereof.

Mixed Gas Flow

The gas flow for preparing calibrated microvesicles according to the method of the invention comprises a mixture of the gaseous compounds illustrate above, in the above illustrated respective volume ratios.

Figure 4:
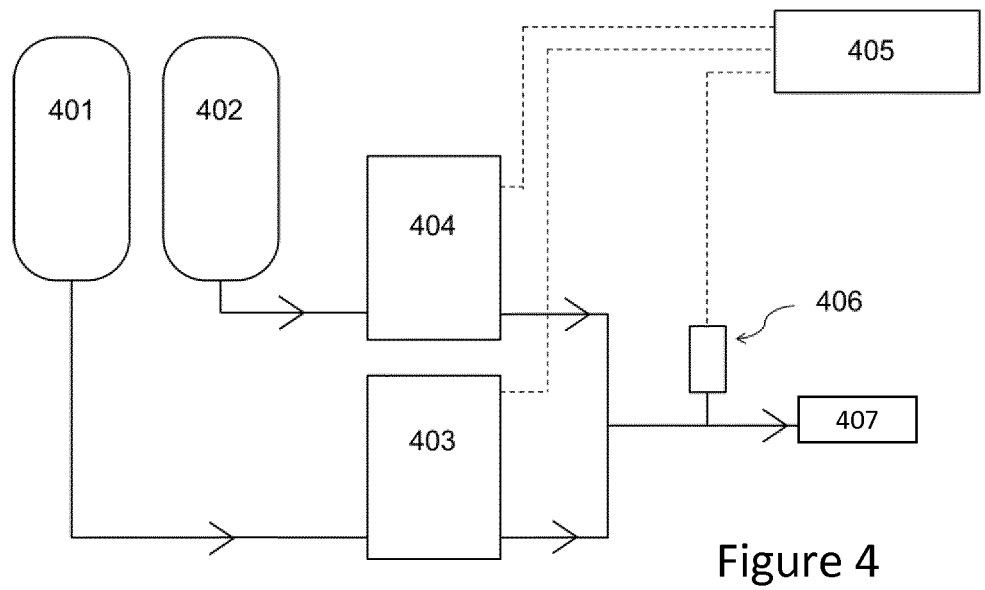
FIG. 4 shows a schematic example of a gas-mixer.

FIG. 4 shows a schematic gas-mixing device useful in a process according to the invention. A gas mixing device comprises two gas containers 401 and 402, each filled with a HS gas and with a LS gas, respectively. The flow of each gas is regulated by corresponding mass flow controllers (MCFs), 403 and 404, respectively. The MCFs are controlled by a control unit 405 (e.g. a customized software program implemented in a programming language such as LabView, National Instruments, or Matlab, Mathworks, and installed on a personal computer) in order to set and keep the desired mixing ratio. A pressure sensor 406 measures the actual pressure in the output channel containing the gas mixture which leads to the microfluidic chip 407, where microvesicles are formed. In this way a desired gas flow operating the microfluidic chip can be controlled and adjusted according to the desired setting, and the MCF's can be regulated accordingly to maintain the same mixing ratio. A devise as illustrated in FIG. 4 can be used for accurately mixing the two gases, having substantially different aqueous solubility, under conditions particularly required for the formation of microvesicles by microfluidic flow focusing. In this way, highly stable calibrated microvesicles can be manufactured in a reproducible way with an optimal PDI, an optimal yield and without the presence of foam-forming large bubbles.

Advantageously, the preparation method illustrated in co-pending application PCT/EP2017/071788, where the temperature of freshly formed microvesicles is controlled in order to limit coalescence, can be used.

Figure 1:
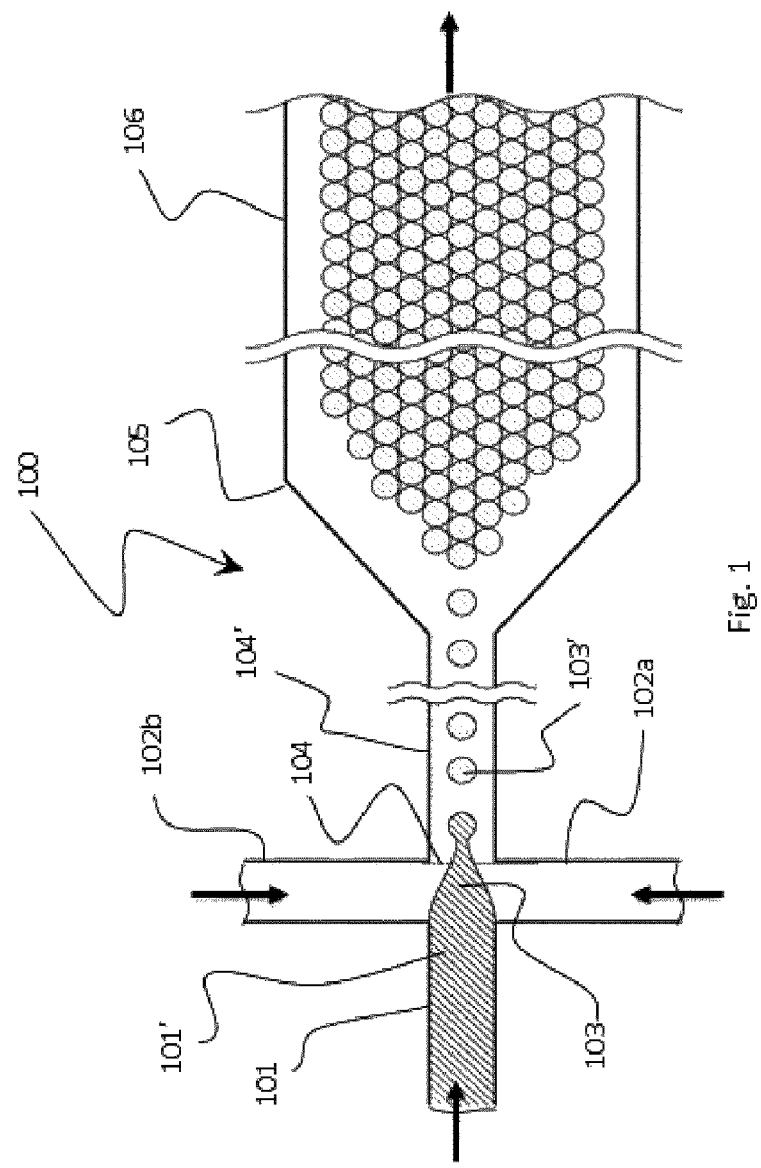
FIG. 1 is a schematic representation of the core portion of a microfluidic flow-focusing device.

FIG. 1 shows a schematic representation of the core portion 100 of a flow-focusing device ("microfluidic chip") useful in the process of the invention. The chip comprises a first feed channel 101 for feeding the (mixed) gaseous flow 101' and two additional feed channels 102a and 102b for supplying the liquid flow containing the amphiphilic material.

The mixed gas flow and the two liquid flows are directed towards the contact zone 103 and then through the calibrated orifice 104, shown as a dotted line in FIG. 1. The calibrated orifice is connected to a calibrated channel 104' having preferably the same cross-section as the orifice, which is in turn connected to an initial portion 105 of the outlet channel 106. In an alternative embodiment (not shown) the calibrated orifice 104 may be a nozzle directly connected to the initial portion 105 of outlet channel 106 i.e. without the calibrated channel in-between. The microvesicles 103' are formed in the calibrated orifice and directed, through calibrated channel 104', to the initial portion 105 of the outlet channel 106. The hydraulic diameter of the outlet channel is generally larger than the hydraulic diameter of the calibrated orifice and typically increases from the initial diameter of the calibrated orifice to the final diameter of the outlet channel 106, corresponding substantially to the hydraulic diameter of a collecting tube (not shown), connecting the flow-focusing device to a container, e.g. a sealed vial for collecting the suspension of microvesicles.

The undesired coalescence phenomenon of microvesicles possibly occurring in the initial portion of the outlet channel may be substantially reduced by controlling the temperature of the microvesicles in the initial portion 105 of the outlet channel of the device and preferably also in the contact zone 103 and in the calibrated orifice 104.

In particular, the initial portion of the outlet channel is preferably kept at a temperature of not less than 20% lower with respect to the transition temperature ($T_m$) of the amphiphilic material contained in the liquid flow and forming the stabilizing envelope of the microvesicles. More preferably, said temperature is not less than 10% lower with respect to the $T_m$ of the amphiphilic material. While in general it is not necessary to have a temperature excessively higher than the $T_m$, such temperature may be as high as necessary, compatibly with the heat degradation resistance of the amphiphilic materials; for instance, the temperature may be up to 20% higher than the $T_m$ of the amphiphilic material, preferably up to 10% higher. In preferred embodiments, said temperature is at or slightly above (e.g. up to 5° C. higher) the $T_m$ of the amphiphilic material. The temperature control is particularly useful in the zone of the outlet channel where the flow of the aqueous suspension of microvesicles has not yet reached a substantial stationary velocity, e.g. when the absolute velocity gradient is higher than about $10\ s^{-1}$. Depending on the geometry of the chip, said zone may extend for a length of from about 0.1 mm to 100 mm from the calibrated orifice, preferably from 1.0 to 50 mm and more preferably from 2.0 to 30 mm.

Advantageously, the temperature may similarly be controlled by applying the parameters specified above also to the contact zone and to the calibrated orifice (and, where present, to the calibrated channel).

The applied controlled temperature provides a substantial reduction of the coalescence among the formed microvesicles.

As shown in detail in the experimental part, by keeping the temperature at or around the $T_m$ of the amphiphilic material, a reduced coalescence is observed by using substantially lower concentrations of amphiphilic materials (as compared to the higher concentrations necessary where no heating is applied).

The flow-focusing device can be any of those known in the art, described for instance in (see e.g. Ref. 3). Preferably the flow focusing device comprises a chip, such as the one described e.g. in Ref. 4.

Figure 2:
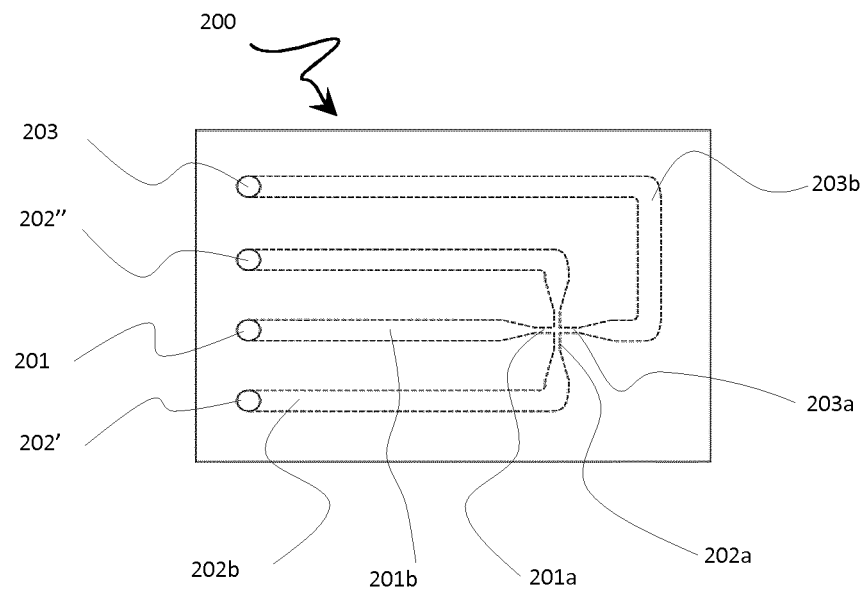
FIG. 2 shows an exemplary schematic representation (top view) of a microfluidic device useful for the flow-focusing process of the invention.

With reference to the schematic drawing of FIG. 2, the chip 200 may comprise a first inlet channel 201 through which the gas mixture flow is supplied and two inlet channels 202' and 202" through which the liquid flow is supplied. Each of said inlet channels is connected to a respective reservoir through respective tubing (not shown). The chip further comprises an outlet channel 203 connected through a respective tubing to a container (not shown) adapted for collecting the suspension of microvesicles. The cross-section of the final portion of the inlet channels 201a and 202a, close to the calibrated orifice, is substantially reduced with respect to the remainder of the channel 201b and 202b. The cross-section of this final portion 201a and 202a may vary from 25 to $1·10^4\ \mu m^2$, preferably from 200 to $1·10^3\ \mu m^2$, advantageously corresponding substantially to the cross-section of the calibrated orifice. The cross-section of the initial portions of the inlet channels may vary from $1·10^3$ to $1·10^6\ \mu m^2$, preferably from $1·10^4$ to $1·10^5\ \mu m^2$, while their length may vary from 50 mm to 1 mm, preferably from 2 mm to 5 mm. Similarly, the cross-section of the initial portion 203a of the outlet channel (corresponding to the calibrated channel in FIG. 1) is also relatively reduced; its section is generally calibrated according to the desired diameter of the microvesicles to be prepared (see e.g. Ref. 4). For instance, for preparing monodispersed microvesicles with a mean diameter of 5 μm, the calibrated orifice and the calibrated channel will have a cross-sectional area of about 250 to 2500 μm². Advantageously, the cross-sections of the inlet channels and that of the outlet channel are substantially the same, as well as that of their respective final and initial portions. The length of the calibrated channel 203a may vary from about 0.05 mm to about 10 mm, preferably from 1 mm to 5 mm, while the total length of the outlet channel may be up to 100 mm, preferably up to 50 mm and more preferably up to 30 mm. Typically, the chip is made out of two halves of quartz glass, fused silica, or any plastic (e.g. Poly(methyl methacrylate)) material. The channels can be produced by etching, either dry or wet, the internal surface of each half, for the whole desired depth and width. For instance, the surface may be etched at a constant depth of 14 μm and with a width of 15-20 μm for the respective calibrated portions close to the contact zone and a width of 0.5-1.0 mm for the remainder portions. Commercially available chips suitable for the use in the process of the invention are available for instance from Dolomite microfluidics (Royston, United Kingdom) or Micronit (Enschede, the Netherlands).

According to a preferred embodiment, in order to maintain the monodispersity of the formed microvesicles, the suspension may then rapidly be cooled down to a temperature below the $T_m$ of the amphiphilic material, preferably once the flow of the suspension in the collection zone has reached a substantially stationary velocity.

Figure 3:
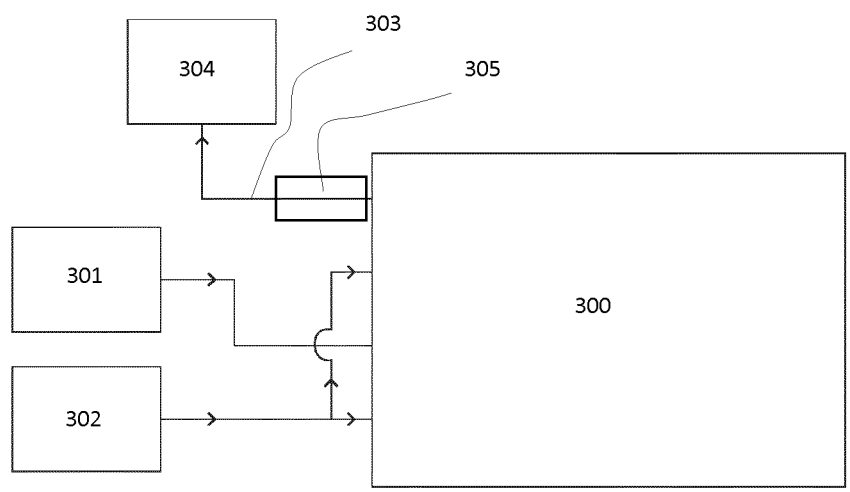
FIG. 3 shows an exemplary schematic drawing of a device useful for the process of the invention.

With reference to FIG. 3, a unit 300 (e.g. a chip as described in FIG. 2) comprising the core portion of a flow-focusing device may be kept at the desired temperature close or slightly above the $T_m$ of the amphiphilic material, as described above, e.g. by means of a thermostatic bath. The gas flow and the liquid flows comprising the amphiphilic material are supplied to unit 300 from respective gas-mixing device 301 (e.g. like the one illustrated in FIG. 4) and reservoir 302 to the unit 300 via respective supply tubing (with an internal diameter of e.g. 100 to 1000 μm preferably from 150 to 250 μm). The outlet tubing 303 connects the outlet channel (not shown) of unit 300 to a suitable collecting container 304, e.g. a sealed vial. It is generally advantageous to begin the cooling of the suspension of microvesicles within few seconds from the formation of the microvesicles, preferably as soon as the flow of the suspension reaches a substantially stationary velocity. Typically, said cooling may be initiated within 180 seconds from the formation of the microvesicles, preferably within 60 seconds, more preferably within 10 seconds and even more preferably within 2 seconds. Depending on the geometry of the flow-focusing device, the stationary flow is generally reached within few milliseconds or even less after the microvesicles formation; the cooling may thus be applied starting from 1 milliseconds after the formation of the microvesicles. As typically the suspension of microvesicles reaches the exit of unit 300 within less than few milliseconds after formation, the cooling may advantageously be applied to the initial portion of the outlet tubing exiting the unit 300. Thus, an initial portion of the outlet tubing is advantageously subjected to cooling by suitable cooling means 305, e.g. a heat exchanger, in order to reduce the temperature of the suspension of gas-filled microvesicles below $T_m$ of the amphiphilic material forming the stabilizing envelope of the microvesicles. The length of the initial portion of the outlet tubing subjected to the cooling may vary e.g. from 1 cm to 100 cm, preferably from 5 cm to 10 cm, depending, for instance from the heating temperature of the unit 300, the efficacy of the applied cooling, the contact time and so on.

The container 304 where the microvesicles suspension is collected is preferably a (glass) vial, generally with a sealed closure (e.g. a rubber stopper). Said container is preferably prefilled with the same LS gas used in the manufacturing process, at ambient pressure. A venting device (e.g. a needle) is preferably inserted into the container in order to equalize the overpressure generated by the liquid filling of the vial.

When referring herein to the transition temperature $T_m$ of an amphiphilic material, said temperature may be referred either to a single amphiphilic component or to a mixture of amphiphilic components.

In particular, when the amphiphilic material forming the stabilizing envelope is a mixture of different amphiphilic components, said $T_m$ is generally referred to as the $T_m$ of said mixture of amphiphilic components. For a mixture of amphiphilic materials, the measured $T_m$ generally corresponds to a molar ratio weighted mean of the $T_m$ of the individual components of the mixture.

The $T_m$ of an aqueous lipid mixture may advantageously be measured by using differential scanning calorimetry (DSC). Measurements of $T_m$ of amphiphilic materials (pure or mixtures), including phospholipids, can be performed for instance by using a DSC-Q2000 device (TA Instruments, New Castle, Del. USA). Parameters such as the temperature at which the transition starts and reaches its peak and the enthalpy of the transition are measured to determine the $T_m$. Details of the measurements are provided in the experimental part.

Figure 5:
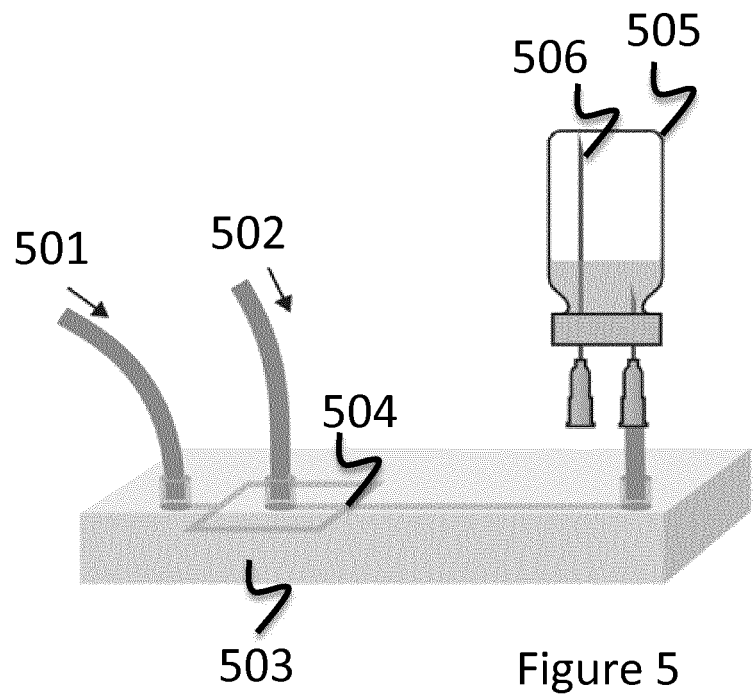
FIG. 5 shows an illustrative example of a set-up for the manufacturing method of the invention.

FIG. 5 shows an example of a microfluidic flow focusing device used for the production of calibrated microvesicles. A gas flow 502 comprising a mixture of a LS gas and a HS gas (e.g. from the mixing device of FIG. 4), and a liquid flow 501 (comprising an amphiphilic material, e.g. a phospholipid, fatty acid or mixtures thereof), are supplied to microfluidic chip 503 to produce microvesicles through orifice 504. The microvesicles suspension is collected in a vial 505, which is preferably prefilled with the LS gas at ambient pressure. A venting device (e.g. a needle 506) is preferably used to equalize the overpressure generated by the liquid filling of the vial. At the end of the collection of the microvesicles suspension, the venting device is preferably removed and the container is preferably sealed to avoid further gaseous exchange with the external atmosphere.

Use

The microvesicles prepared according to the method of the invention may be used in a variety of diagnostic and/or therapeutic techniques, including in particular Ultrasound and Magnetic Resonance.

Diagnostic techniques include any method where the use of the gas-filled microvesicles allows enhancing the visualisation of a portion or of a part of an animal (including humans) body, including imaging for preclinical and clinical research purposes. A variety of imaging techniques may be employed in ultrasound applications, for example including fundamental and harmonic B-mode imaging, amplitude modulation, pulse or phase inversion imaging and fundamental and harmonic Doppler imaging; if desired three-dimensional imaging techniques may be used.

Microvesicles for diagnostic use may be administered (e.g. by injection) at a concentration of from about 0.01 to about 1.0 μL of gas per kg of body weight, depending e.g.

on their respective composition, the tissue or organ to be imaged and/or the chosen imaging technique. This general concentration range may of course vary depending on specific imaging applications, e.g. when signals can be observed at very low doses such as in amplitude modulation and pulse inversion imaging.

Possible other diagnostic imaging applications include scintigraphy, light imaging, and X-ray imaging, including X-ray phase contrast imaging.

Therapeutic techniques include any method of treatment (as above defined) of a patient which comprises the use of microvesicles either as such (e.g. ultrasound mediated treatment of ischemic stroke, clot lysis etc.) or in combination with a therapeutic agent (e.g. for the delivery of a bioactive compound to a selected site or tissue, such as in drug delivery, gene therapy or in the use as vaccine), and which is capable of exerting or responsible to exert a biological effect in vitro and/or in vivo, either by itself or upon specific activation by various physical methods (including e.g. ultrasound mediated delivery).

Microvesicles for therapeutic treatments may typically be administered in a concentration of from about 0.01 to about 5.0 µL of gas per kg of body weight, depending e.g. from their respective composition, the type of subject under treatment, the tissue or organ to be treated and/or the therapeutic method applied.

The following examples will help to further illustrate the invention.

EXAMPLES

Materials

| | | |
|---|---|---|
| DPPC | dipalmitoyl-phosphatidylcholine | (1) |
| DSPC | distearoyl-phosphatidylcholine | (1) |
| DPPA | dipalmitoyl phosphatidic acid | (1) |
| DPPE-PEG5000 | Dipalmitoylphosphatidylethanolamine-polyethyleneglycol5000 | (1) |
| $C_3F_8$ | Octafluoropropane | (2) |
| $C_4F_{10}$ | Perfluorobutane | (2) |
| $CO_2$ | Carbon Dioxide | (3) |

(1) CordenPharma International, Plankstadt, German; y
(2) F2 Chemicals Ltd, Preston, United Kingdom;
(3) Carbagas, Lausanne, Switzerland Example 1

Preparation of Gas-Filled Microvesicles

Microvesicles were synthesized using a commercially available microfluidic flow-focusing device (Dolomite microfluidics, small droplet chip, 14 µm etch depth, part no. 3200136), mounted in a commercially available chip holder (Dolomite microfluidics, part numbers: 3000024, 3000109, 3000021) allowing for the leak tight connection of the chip to the gas and liquid supply tubing (Peek Upchurch, 1/16 inch O.D, 150 µm I.D.). The microvesicles formation channel had a width of 17 µm and a length of 135 µm. The overall channel depth was 14 µm. The chip and its holder were positioned in an optically transparent temperature controlled water bath that was mounted on an inverted microscope equipped with a 20 times magnification objective (Olympus, LMPLAN 20×) and a CCD camera (Lumenera, LM156M). The temperature of the thermostatic bath was set at 50° C. (corresponding to a temperature slightly lower than the transition temperature of the mixture of amphiphilic materials in the liquid flow).

The amphiphilic materials in the liquid flow were:
DSPC:DPPE-PEG5000 in a respective molar ratio of 9:1. The Tm for the mixture was experimentally determined to be 55° C.

The materials were added with the above molar ratios at a concentration of 20 mg/mL to a 2:1 (volume ratio) chloroform/methanol mixture under stirring at 60° C. until complete dissolution of the amphiphilic material. The solvent was then evaporated under reduced pressure and the obtained film was dried overnight under reduced pressure. The dried material was then redispersed (at concentrations of 15 mg/mL) in saline (0.9% NaCl) at 60° C. under stirring for 30 minutes. The dispersion was then sonicated by using a tip sonicator (Branson Sonifier 250) to homogenously disperse the material. The preparations were then filtered using a polycarbonate filter (0.45 µm pore size), cooled down to room temperature and degassed.

Gas-filled microvesicles with variable volume ratios of a HS gas and LS gas were prepared with a gas-mixing device similar as shown schematically in FIG. 4. Briefly, two gas containers were filled with $CO_2$ as HS gas and $C_3F_8$ as a LS gas, respectively. The gas flow of each gas was regulated by respective mass flow controllers: (i) EL-Flow: F200CV-002-RAD-11-K, for the HS gas and (ii) Low-ΔP-Flow: F-200DV-RAD-11-Z for the LS gas, (both gas controllers from Bronkhorst, Ruurlo, The Netherlands). The mass flow controllers were controlled by a customized software program implemented in Matlab (Mathworks), which was installed on a personal computer, in order to set and keep the desired mixing ratio. A pressure sensor (PSE530-M5-L; SMC Corp., Tokyo, Japan) measured the actual pressure in the gas mixture in the outlet channel leading to the microfluidic chip; a gas pressure of 1.8 bar was used for the formation of the microvesicles. The liquid co-flow rate was controlled by using a separate mass flow controller (Mini Cori Flow: M13V14I-MAD-11-K-S; Bronkhorst, Ruurlo, The Netherlands). A liquid co-flow rate of around 140 µL/min was used to operate the flow-focusing device in the jetting regime and produce microvesicles with a diameter (mode) of around 4 µm.

The microvesicle suspension was then collected in a sealed vented vial saturated with $C_3F_8$.

For the various preparations, the relative height of the foam layer formed above the liquid suspension collected in the vial was measured, as a relative percentage of the height of the liquid suspension. The results are illustrated in table I below.

TABLE I

Percentage of insoluble gas vs. Foam height

| Prep. No. | Volume % $C_3F_8$ | Foam layer height (%) |
|---|---|---|
| 1 | 2 | 1 |
| 2 | 7 | 1 |
| 3 | 10 | 1 |
| 4 | 13 | 2 |
| 5 | 20 | 4 |
| 7 | 30 | 7 |

As inferable from the above table, a volume amount of LS gas higher than 20% substantially increases the undesirable foam formation above the aqueous suspension of gas-filled microvesicles. On the other side, amounts of LS gas of 13% or lower, preferably of 10% or lower substantially reduce the foam formation.

Example 2

Determination of the Pressure Resistance and LS Gas Concentration

The preparations of example 1 were repeated by replacing $C_3F_8$ with $C_4F_{10}$ as LS gas. Three preparations with 5% $C_4F_{10}$ and two preparations with 13% $C_4F10$ gas were tested for the pressure resistance of the gas-filled microvesicles according to the following procedure. Pressure resistance is determined from optical absorbance measurement as a function of hydrostatic overpressure. The hydrostatic overpressure (expressed in mmHg; 1 mmHg=133.3 Pascals) corresponding to 50% of the absorbance measured at 0 mmHg overpressure is considered as the pressure resistance value, or Pc50.

Absorbance was measured using a modified spectrophotometer (Jenway 6300, Barloworld Jenway, Stone, UK) at a wavelength of 700 nm. Quasi-static compression was applied to a suspension of microbubbles, confined in an air-tight cuvette, through overpressure increasing at a rate of 4.2 mmHg/s, using compressed air regulated by a proportional valve (T2000, Marsh Bellofram, Newell, W. Va.) which was controlled by an in-house developed software program written in LabView (National Instruments, Austin, Tex.).

The Pc50 measured for the three preparations with 5% of $C_4F_{10}$ ranged between 600 and 780 mmHg, while the Pc50 measured for the two preparations with 13% of $C_4F_{10}$ ranged between 705 and 727 mmHg, thus showing a comparable resistance to pressure for the different preparations.

The concentration of LS gas in the final stabilized microbubbles was also measured according to the following procedure. Microvesicles suspension volumes of 1 mL were injected in a separate sealed vial, sonicated for 60 minutes to destroy all the microvesicles and let to rest for 1 hour. The amount of LS gas in the headspace was then measured by gas chromatography.

The final concentration of $C_4F_{10}$ in stabilized microbubbles prepared with a concentration of 5% of $C_4F_{10}$ and 95% of $CO_2$ was of 50%, while the final concentration of $C_4F_{10}$ in microbubbles prepared with a concentration of 13% of $C_4F_{10}$ and 87% of $CO_2$ was of 70%.

Example 3

Preparation of Aqueous Dispersions of Amphiphilic Material

Two mixtures of amphiphilic materials with different phase transition temperatures ($T_m$) were used:

M1: DSPC:DPPA:DPPE-PEG5000 ($T_m$=55° C.)
M2: DPPC:DPPA:DPPE-PEG5000 ($T_m$=44° C.)
both in a molar ratio of 8:1:1.

The materials were added with the above molar ratios at a concentration of 20 mg/mL to a 2:1 (volume ratio) chloroform/methanol mixture under stirring at 60° C. until complete dissolution the amphiphilic material. The solvent was then evaporated under reduced pressure and the obtained film was dried overnight under reduced pressure. The dried material was then redispersed (at concentrations of from 5 to 15 mg/mL, as detailed in the part "preparation of microvesicles") in a mixture of glycerol, propylene glycol, and water (GPW, volume ratio of 5:5:90) at 60° C. under stirring for 30 minutes. TRIS buffer (20 mM) was added to adjust the pH value at 7. The dispersion was then sonicated by using a tip sonicator (Branson Sonifier 250) to homogenously disperse the material. The preparations were then filtered using a polycarbonate filter (0.45 μm pore size), cooled down to room temperature and degassed.

Measurement of Transition Temperature

Transition temperatures of amphiphilic materials (pure DPPC or DSPC and mixtures of DPPC:DPPA:DPPE-PEG5000 or DSPC:DPPA:DPPE-PEG5000) were determined by using commercial Differential Scanning Calorimetry DSC-Q2000, with Tzero aluminum crucibles (TA Instruments, New Castle, Del. USA). System calibration, including temperature and heat flow, was carried out with Indium metal (enthalpy of fusion 28.71 J/g±0.5 J/g; onset temperature of fusion 156.6° C.±0.25° C.).

Dispersions of the amphiphilic material (pure or mixtures) in GPW/TRIS were prepared according to the procedure described above for the DSC measurements (about 30 μL each, concentration 10 mg/mL).

DSC measurements were carried out by heating at a constant temperature rate of 2° C./min over a temperature range from 20° C. to 80° C. Nitrogen was used as purging gas at a flow rate of 50 mL/min.

The results are illustrated in the table II below.

TABLE II

| | Transition temperatures | |
| --- | --- | --- |
| | Starting transition temperature (° C.) | Transition peak $T_m$ (° C.) |
| DPPC | 40 | 42 |
| DSPC | 52 | 55 |
| DPPC/DPPA/DPPE-PEG5000 | 41 | 44 |
| DSPC/DPPA/DPPE-PEG5000 | 52 | 55 |

Example 4

Preparation of Gas-Filled Microvesicles

Microvesicles were synthesized using the same microfluidic chip as described in example 1. The liquid co-flow rate was controlled using a syringe pump (Harvard PHD4400). The gas ($SF_6$) was pressure controlled using a pressure regulator (Omega, PRG101-25) connected to a pressure sensor (Omega, DPG1000B-30G). Individual microvesicles were automatically detected from the recorded optical images to measure their sizes offline on a PC using Matlab software (The Mathworks Inc., Natick, Mass.). Differently from example 1, two different liquid co-flow rates were tested (45 μL/min or 55 μL/min) to operate the flow-focusing device under the dripping regime or under the more preferred jetting regime, respectively.

The microvesicle suspension was collected in a sealed vial and stored at room temperature.

Effects of Heating the Formed Microvesicles

FIGS. 9a to 9e show the results obtained using a liquid co-flow of the DSPC/DPPA/DPPE-PEG5000 suspension ($T_m$ 55° C.) as prepared above, with concentrations of amphiphilic material ranging from 5 to 15 mg/mL (FIG. 9a-9e, respectively) and at different temperatures of the thermostatic bath containing the microfluidic chip (similar to the one illustrated in FIG. 2). Squares (■) indicate experiments conducted under the dripping regime, while triangles (▲) indicate experiments conducted under the more preferred jetting regime.

Figure 9:
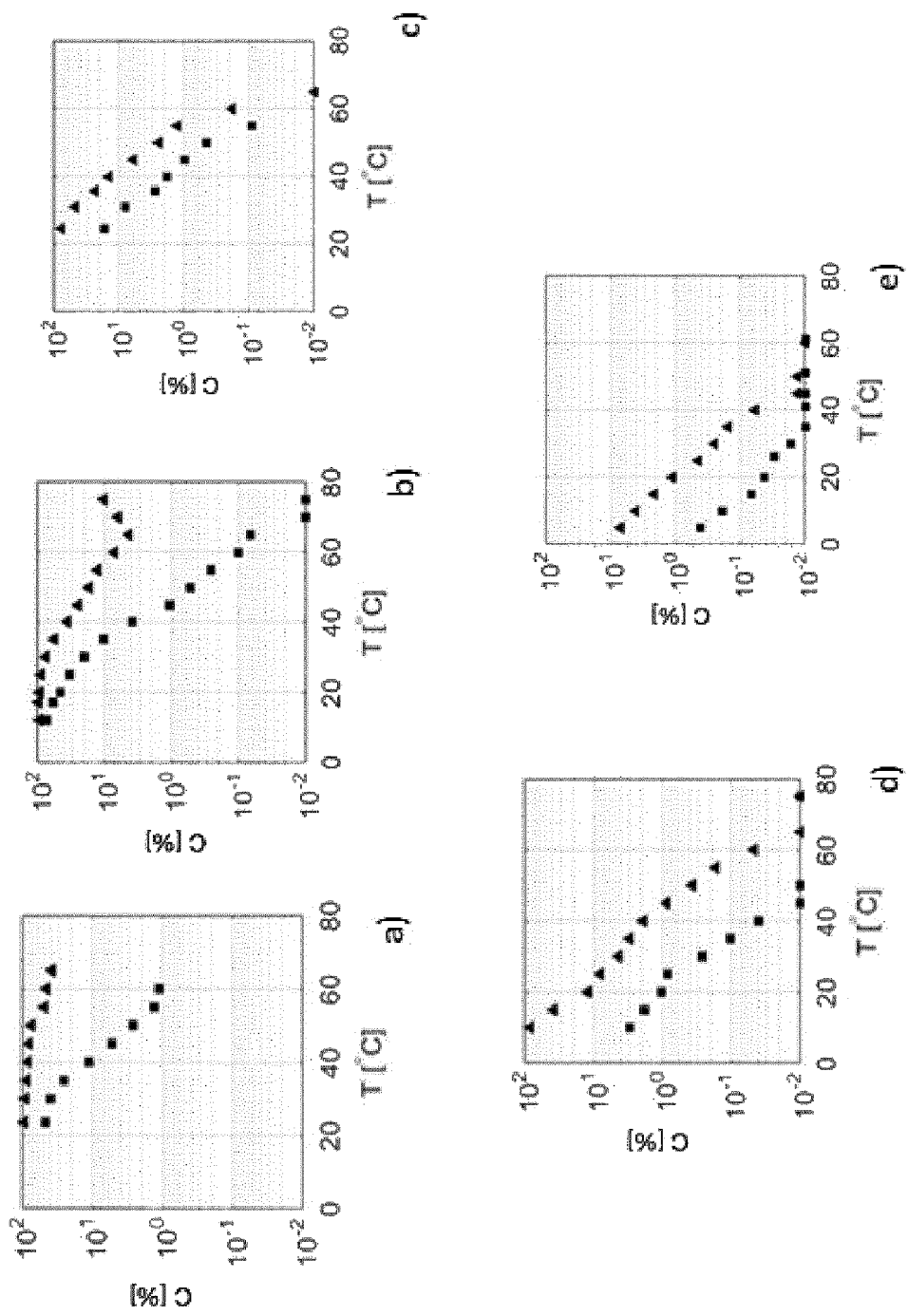
FIG. 9 illustrates experimental results of the temperature control during the formation of gas-filled microvesicles according to the invention.

As can be observed in these figures, the percentage of coalescence (C [%]) of microvesicles is generally lower in the dripping regime compared to the jetting regime. In addition, under both dripping and jetting regimes, the advantageous effect of reducing coalescence by increasing the temperature is apparent. Considering in particular the jetting regime, for concentrations of 7.5 mg/mL (FIG. 9b) increasing the temperature to the $T_m$ of the amphiphilic mixture (55° C.), or higher, results in a coalescence of microvesicles of about 10% or lower. Still focusing on the jetting regime, the same heating to or above the $T_m$ of the amphiphilic material provides a coalescence of less than 1% for concentrations of the amphiphilic material of 10 mg/mL (FIG. 9c). By increasing the concentration of the amphiphilic material to 15 mg/mL (FIG. 9e), similar results can be obtained at room temperature. Note that in this case the concentration of the amphiphilic material needs to be increased by 50%.

These results thus demonstrate that by keeping the temperature around the $T_m$ of the amphiphilic material, a reduction of the coalescence effect can be obtained (as compared to higher coalescence measured for the same preparation at lower temperatures). The results further show that by keeping the temperature around the $T_m$ of the amphiphilic material, similar percentages of coalescence may be obtained by using substantially lower concentrations of amphiphilic materials (as compared to the higher concentrations needed if no heating is applied).

Figure 10:
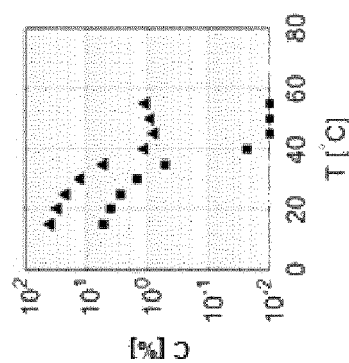
FIG. 10 illustrates experimental results of the temperature control during the formation of gas-filled microvesicles with other amphiphilic materials according to the invention.

FIG. 10 shows the results obtained using a liquid co-flow of the DPPC/DPPA/DPPE-PEG5000 suspension ($T_m$ 44° C.) as prepared above, with concentrations of amphiphilic material of 10 mg/mL at different temperatures of the thermostatic bath. Similarly, to the results discussed above, also in this case a coalescence of 1% or less is obtained when heating to a temperature close or higher than the $T_m$ of the amphiphilic material.

Effects of Downstream Cooling the Suspension

To evaluate the effects of downstream cooling on the dispersity of the microvesicles, different cooling conditions were tested.

According to setup A (early-cooled suspension), the suspension was passed through a heat exchanger (at 20° C.) 3 ms after microvesicle formation, to suddenly reduce the temperature of the suspension below $T_m$, particularly at room temperature. Accordingly, the tubing exiting from the chip in the thermostatic bath was passed through a heat exchanger after approximately 0.5 mm from the chip's exit.

According to setup B (late-cooled suspension), the suspension was passed through the same heat exchanger only 3 minutes after microvesicle formation. Accordingly, in this second configuration, the tubing exiting from the chip was replaced by a tubing with an inner diameter of 1 mm and this tubing was kept in the thermostatic bath for a length of approximately 20 cm and then passed through a heat exchanger.

Figure 11:
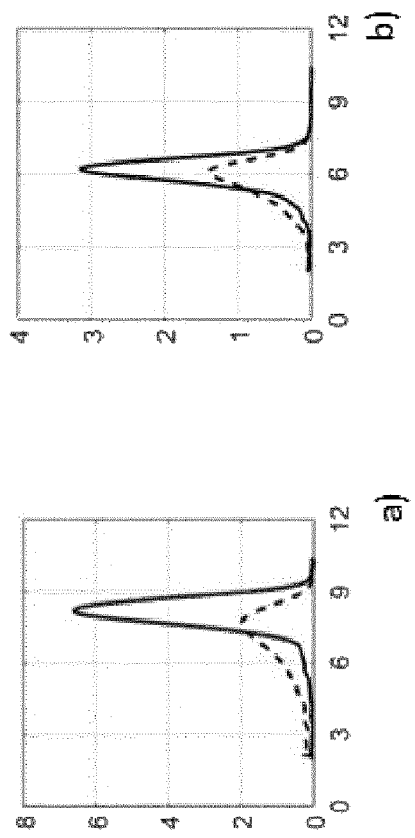
FIG. 11 illustrates experimental results of the cooling effect on a suspension of gas-filled microvesicles.

Both setups were tested at flow rates of 55, 65 and 75 µL/min and the results are illustrated in FIGS. 11a, 11b and 11c, respectively (X axis=diameter in mm, Y axis=relative count of microvesicles by number). In FIGS. 11a-11c, the dashed lines show the size distributions of late-cooled preparations, while solid lines show the size distributions of early-cooled preparations. It is apparent from these figures that the PDI of the early-cooled suspension is lower compared to the one of the corresponding late-cooled suspension. Moreover, it can be appreciated from these figures that the mean size of the microvesicles decrease with increasing flow velocity.

Similar results may be obtained with other mixtures of amphiphilic materials, particularly those combinations of amphiphilic materials previously illustrated.

CITED REFERENCES

1 T. Segers et al. ("Stability of monodisperse phospholipid-coated microbubbles formed by flow-focusing at high production rates," Langmuir 32(16), 3937-3944 (2016),
2 R. Shih et al., "Flow-focusing regimes for accelerated production of monodisperse drug-loadable microbubbles toward clinical-scale applications", Lab. Chip 13, 4816-4826 (2013)
3 Intl. Pat. Appl. WO 2013/141695 (Tide Microfluidics et al.)
4 Castro-Hernández, E. et al., "Microbubble generation in a co-flow device operated in a new regime", Lab. Chip. 2011, 11 (12), 2023-9

The invention claimed is:

1. A method for preparing a suspension of gas-filled microvesicles using a microfluidic flow-focusing device which comprises:
   providing (i) a gaseous flow and (ii) an aqueous liquid flow comprising an amphiphilic microvesicle-stabilizing material;
   directing said gaseous flow and said liquid flow through respective inlet channels of the device towards a contact zone;
   directing said gaseous flow and said liquid flow from the contact zone through a calibrated orifice of the device to obtain an aqueous suspension comprising said gas-filled microvesicles; and
   directing said suspension comprising said microvesicles towards an outlet channel of the device;
   wherein said gaseous flow comprises a mixture of a first gas and a second gas, wherein said first gas is selected from the group consisting of air, nitrogen, carbon dioxide and mixtures thereof, said first gas having a solubility in water defined as Bunsen Coefficient, α, higher than 0.01 and a molecular weight lower than 80 Daltons and said second gas being a biocompatible perfluorinated gas having a solubility in water defined as Bunsen Coefficient, α, of 0.001 or lower and a molecular weight higher than 120 Daltons, the volume percentage of said second gas in said gaseous flow being of from 18% to 2%; and wherein the obtained gas-filled microvesicles contain a final amount of said second gas of at least 45% by volume.

2. The method according to claim 1 wherein, the volume percentage of said second gas in said gaseous flow is of 15% or lower.

3. The method according to claim 1 wherein, the volume percentage of said second gas in said gaseous flow is of 13% or lower.

4. The method according to claim 1 wherein the volume percentage of said second gas is of at least 5%.

5. The method according to claim 1 wherein said first gas has a solubility in water higher than 0.5.

6. The method according to claim 1 wherein said second gas has a solubility in water of 0.0008 or lower.

7. The method according to claim 6 wherein said second gas has a solubility in water of 0.0005 or lower.

8. The method according to claim 1 wherein said perfluorinated gas is selected from the group consisting of $SF_6$, $CF_4$, $C_2F_6$, $C_3F_8$, $C_4F_8$, $C_4F_{10}$ and mixtures thereof.

9. The method according to claim 1 wherein said gas is carbon dioxide.

10. The method according to claim 1 wherein the said final amount of said second gas is of at least 60% by volume.

11. The method according to claim 1 wherein said amphiphilic microvesicle-stabilizing material is a phospholipid.

12. The method of claim 11 wherein said amphiphilic material is dispersed in an aqueous carrier at a concentration of from 5.0 to 20 mg/mL.

13. The method according to claim 5 wherein said second gas has a solubility in water of 0.0008 or lower.

14. The method according to claim 13 wherein said second gas has a solubility in water of 0.0005 or lower.

\* \* \* \* \*